United States Patent [19]

Snail

[11] Patent Number: 4,815,858
[45] Date of Patent: Mar. 28, 1989

[54] REFLECTOMETERS

[75] Inventor: Keith A. Snail, Washington, D.C.

[73] Assignee: The United States of America as represented by the Secretary of the Navy, Washington, D.C.

[21] Appl. No.: 106,469

[22] Filed: Oct. 9, 1987

[51] Int. Cl.$^4$ ............................................. G01N 21/47
[52] U.S. Cl. .................................... 356/446; 350/619
[58] Field of Search ................ 356/446, 236; 350/618, 350/619

[56] References Cited

U.S. PATENT DOCUMENTS

| | | | |
|---|---|---|---|
| 804,996 | 11/1905 | Anthony | 350/619 |
| 2,852,693 | 9/1958 | Hughes et al. | 356/446 |
| 3,277,773 | 10/1966 | White | 356/446 |
| 3,923,381 | 12/1975 | Winston | 350/293 |
| 3,957,031 | 5/1976 | Winston | 126/270 |
| 4,002,499 | 1/1977 | Winston | 136/206 |
| 4,003,638 | 1/1977 | Winston | 350/293 |
| 4,045,246 | 8/1977 | Winston et al. | 136/89 PC |
| 4,095,905 | 6/1978 | Kuni et al. | 356/446 |
| 4,320,442 | 3/1982 | McComy | 356/446 |
| 4,360,275 | 11/1982 | Louderback | 356/446 |
| 4,691,077 | 9/1987 | Gregory et al. | 250/492.2 |
| 4,693,601 | 9/1987 | Dabelstein et al. | 356/446 |

OTHER PUBLICATIONS

Brandenburg–Focusing Properties of Hemispherical and Ellipsoidal Mirror Reflectometers: Journal of the Optical Society of America, vol. 54, No. 10, pp. 1235–1237, Oct. 84.
Snail—New Optical Systems for the Measurement of Diffuse Reflectance; SPIE vol. 643 Infrared, Adaptive, and Synthetic Aperture Optical Systems (1986) pp. 84–92.
Snail—Reflectometer Design Using Nonimaging Optics, Applied Optics (to be published after 13 Oct. 1987).
Gindele et al.—Spectral Reflectance Measurements Using an Integrating Sphere in the Infrared; Applied Optics, vol. 24, No. 12, pp. 1757–1760, Jun. 15, 1985.
Jacquez, et al.—An Integrating Sphere for Measuring Diffuse Reflectance in the Near Infrared; Journal of the Optical Society of America, vol. 45, No. 10, Oct. 1955, pp. 781–785.
Edwards et al.—Integrating Sphere for Imperfectly Diffuse Samples; Applied Optics vol. 51, Nov. 1961, pp. 1279–1288.

Primary Examiner—Richard A. Rosenberger
Attorney, Agent, or Firm—Thomas E. McDonnell; Andrew M. Lesniak

[57] ABSTRACT

Systems for measuring the diffuse reflectances of various samples are constructed to include a primary mirror (e.g., an ellipsoidal mirror) and a secondary mirror (e.g., a compound parabolic concentrator) cooperating with a radiation source and a radiation detector.

10 Claims, 4 Drawing Sheets

REFLECTOMETERS

FIELD OF THE INVENTION

The invention relates to reflectometers that measure diffuse reflectance of samples, to methods for measuring sample diffuse reflectance; and, more particularly, to reflectometers incorporating mirror schemes that direct and redirect electromagnetic energy, especially radiant energy, relative o samples whose reflectances are measured.

BACKGROUND OF THE INVENTION

Reflectometry endeavors to solve measurement problems with solutions that involve considerable sophistication. An existing problem is a need to devise reflectometers, or optical systems, that lend themselves to a more accurate measurement of diffuse reflectance than has been attained to date. This problem is recognized in a paper authored by Keith A. Snail, entitled "New Optical Systems for the Measurement of Diffuse Reflectance," in a book entitled "Infrared, Adaptive, and Synthetic Aperture Optical Systems," R. Barry Johnson, William L. Wolfe, Janet S. Fender, Editors, Proc. SPIE 643, page numbers 84–92 (1986), published not before Oct. 13, 1986. Several solutions to this problem have been devised that form the substance of the invention. Specific solutions to the problem are set forth in the above-referenced paper by Keith A. Snail. This paper is hereby incorporated by reference into this patent application. These and other solutions will be described with reference to several specific embodiments of the invention.

SUMMARY OF THE INVENTION

An object of the invention is to provide one or more novel optical systems, usually called reflectometers, for measuring the diffuse reflectance of various samples, and to take measurements via unique procedures.

Another object of the invention is to provide one or more novel systems, usually called reflectometers, for measuring diffuse reflectances of various samples with a high degree of accuracy; using unique procedures calculated to provide measurements of greater accuracy than heretofore attainable.

The above, and other objects of the invention are achieved by using systems, or reflectometers, that are constructed around mirror systems of two or more mirrors combined with a radiation detector and with a radiation source for providing radiant energy directed onto a sample whose diffuse reflectance is measured by using the detector to measure the total energy of radiation diffusely reflected from the sample and routed to the detector by the mirrors of a mirror scheme.

In one system, constructed in accordance with the invention, radiation irradiating a sample is diffusely reflected by the sample onto a primary mirror, of ellipsoidal configuration, then redirected into a secondary mirror, known as a compound parabolic concentrator, which de-concentrates and re-directs all of the radiant energy to a radiation detector. This system also works in a reverse manner; radiant energy diffusely illuminating the secondary mirror, or compound parabolic concentrator, is concentrated and redirected to the ellipsoidal primary mirror where the energy is redirected onto the sample in a Lambertian manner; the sample diffusely reflecting rays routed to the radiation detector by any suitable means, such as a flat mirror.

In another system, constructed in accordance with the invention, radiation directed at a sample by any suitable means, such as a flat mirror, is diffusely reflected by the sample onto a primary mirror of paraboloidal configuration -this mirror having matched hemi-paraboloids - and is redirected into a second mirror, known as a compound parabolic concentrator, which deconcentrates and re-directs radiation to a radiation detector. This system also works in a reverse manner; radiant energy diffusely illuminating the secondary mirror, is concentrated and redirected to the paraboloidal primary mirror where the energy is redirected onto the sample in a Lambertian manner, the sample diffusely reflecting rays thereafter routed to the radiation detector by suitable means, such as a flat mirror.

In still another system, constructed in accordance with the invention, radiation illuminating a sample, is diffusely reflected by the sample onto a primary mirror of hemispherical configuration, then redirected into a secondary mirror, such as a compound parabolic concentrator, which deconcentrates and redirects the radiant energy to a radiation detector. This system also works in a reverse manner; radiant energy diffusely illuminating the secondary mirror is concentrated and redirected to the primary mirror where the energy is redirected onto the sample in a Lambertian manner; the sample diffusely reflects rays routed to a radiation detector by any suitable means, such as a flat mirror.

Other features, and advantages, of the invention are disclosed or rendered obvious by the following detailed description which is considered together with the accompanying drawings.

BRIEF DESCRIPTION OF THE DRAWINGS

In the drawings, like numerals in FIGS. 2 and 3, in FIGS. 4 and 5, and in FIGS. 6 and 7, refer to like parts.

DESCRIPTION OF THE PREFERRED EMBODIMENTS

Figure 1:
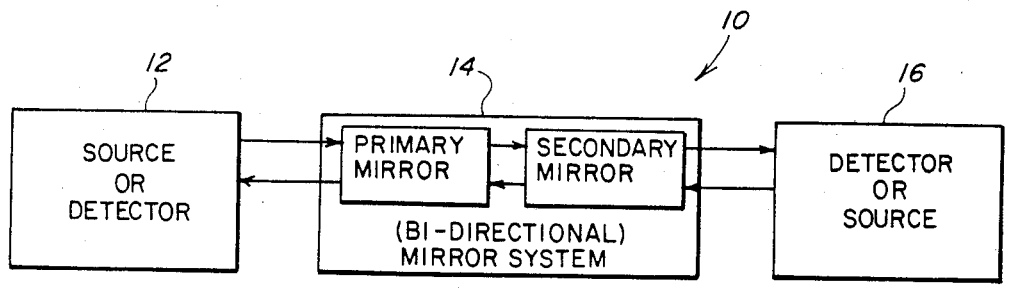
FIG. 1 is a block diagram descriptive of certain systems that may incorporate principles of the invention.

Referring initially to FIG. 1 of the drawings, the block diagram therein represents a system 10, a reflectometer, having features common to the embodiments of the invention that will later be described. These features form a basis for the invention to be described. The block diagram of FIG. 1 is provided merely as an aid to reaching an understanding of the invention, and is not intended to encapsulate the invention which is illustrated by FIGS. 2-7 of the drawings and described by the ensuing discussion of FIGS. 2-7 of the drawings.

In FIG. 1, system 10 comprises certain key components, and may comprise, as shown, main components where one component includes a radiation source, one component includes two (or more) mirrors, and still another component includes a radiation detector, with all these components arranged so that the mirrors serve to link or direct some or all of the radiation from the source to the detector and, in doing so, to provide means to measure sample reflectance.

System 10 is designed so that a sample may be placed in a well defined "location" relative to mirrors, in a system of mirrors, in order to perform diffuse reflectance measurements, using the sample as a test specimen whose reflectance is to be determined with a high degree of accuracy. System 10 is also a system where the "location" itself can be illuminated, in the absence of a sample, with radiant energy to perform system calibration, of a kind that will be familiar to individuals who are experienced in reflectometry.

System 10, typically, includes a radiant energy source, a "bi-directional" multiple-stage mirror system surrounding a location where individual samples are placed, on occasion, and a radiant energy detector. The "bidirectional" design of the mirror system accounts for interchangeability of source and detector locations so that system 10, always includes a mirror system coupling a source to a detector even when no sample is located within system 10.

In FIG. 1, component 12 is identified as a source or detector, component 14 as a (bidirectional) mirror system containing "primary" and "secondary" mirrors, and component 16 as a detector or source to convey the idea of system bidirectionality, which idea is further illustrated by direction arrows indicating that radiation (such as optical rays) can travel through (bidirectional) system component 14 in either of two (opposite) directions, depending on a particular system configuration chosen on a particular occasion. The bidirectional character of system 10 corresponds to "direct" and "reciprocal" modes of operation that will be later described in the context of specific embodiments of the invention. The "direct" mode always involves a sample located at a well defined location in the mirror system i.e. component 14, which is irradiated by a collimated or nearly collimated beam of radiation whereas the "reciprocal" mode always involves a sample in the well defined location in the mirror system that is irradiated in a Lambertian manner with a hemispherical, rather than a collimated source. The invention benefits from the "dual" mode system characteristic but is not limited to "dual" mode systems since "single" mode systems can also embody the invention.

Figure 2:
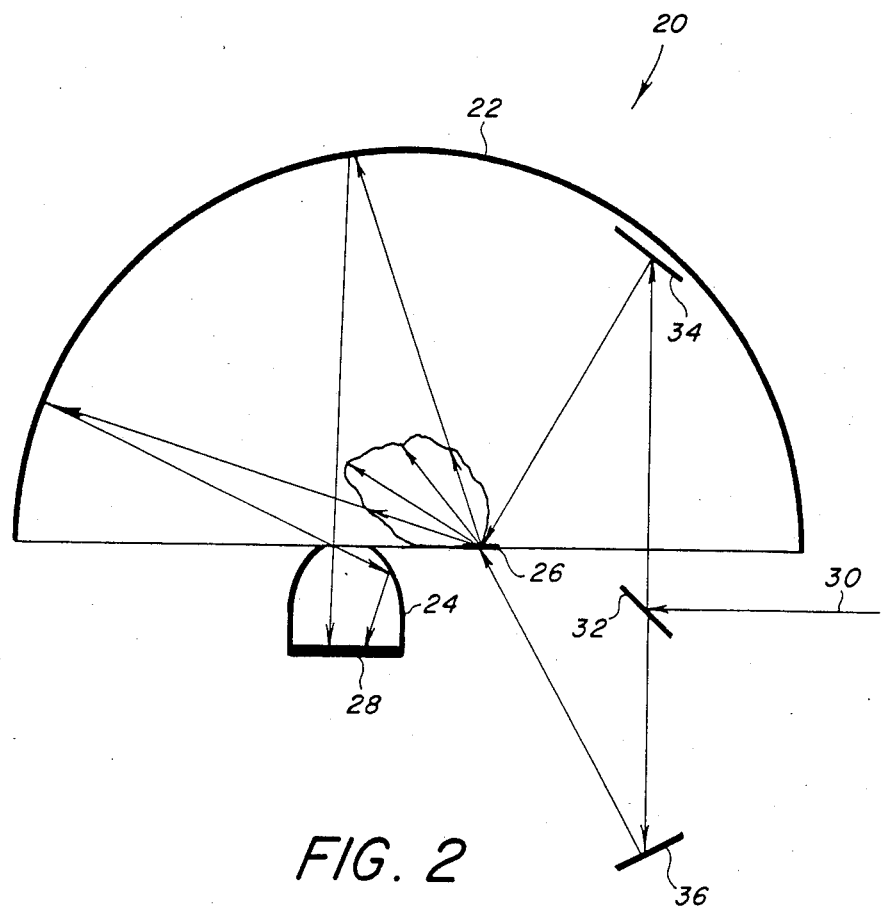
FIGS. 2 and 3 are schematic diagrams of preferred embodiments of the invention incorporating a compound parabolic concentrator (CPC) and an ellipsoidal mirror.
Figure 3:
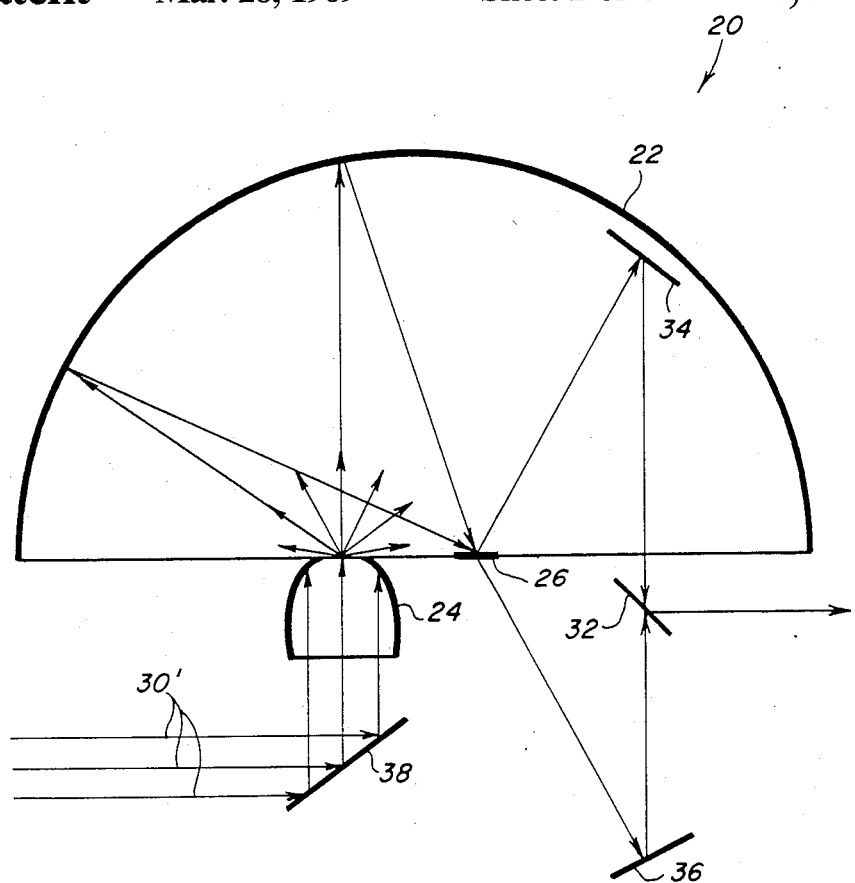

Referring now to FIGS. 2 and 3, an illustrated system 20 representing two closely related embodiments of the invention is shown to be a system operable in two different configurations involving radiation routed through a mirror system 14 in either one or the other of two generally opposite directions, depending on the chosen configuration. System 20, configured as shown in FIG. 2, includes a hemiellipsoidal primary mirror 22, used as a "collector" mirror, a secondary "cavity" mirror 24, used as a "detector" mirror, a sample 26 having an uppermost surface whose diffuse reflectance is to be measured, and a detector 28 receiving radiation (e.g., optical rays) coming from "detector" mirror 24. Mirror 22, mirror 24, sample 26 and detector 28 are in fixed relation to each other to establish a basic system geometry wherein sample "location" is well defined.

A radiation source, represented by a radiation beam 30, produces a beam, coming from the right, that strikes a movable flat mirror 32 where beam 30 is reflected and redirected to another movable flat mirror 34 where beam 30 is again reflected and redirected so that all of the radiation of beam 30 strikes sample 26. Obviously there are other ways of bringing the beam 30 to the sample 26. Sample 26 is carefully located in well defined relation to the location of "detector" mirror 24. Radiant energy such as optical energy of chosen wavelengths, can be employed to comprise beam 30 as a matter of choice but electromagnetic energy of any chosen wavelength or wavelengths can be so employed.

Primary mirror 22 has the function of collecting all, or virtually all, of the radiation after the radiation has been diffusely reflected by a sample such as sample 26. This is illustrated in FIG. 2 by various energy rays shown scattering in many directions from a sample surface to strike the concavity of primary mirror 22 at many points represented by only two points where the rays are reflected toward mirror-detector assembly 24–28. Actually, various rays may strike mirror 22 at all points within the mirror's boundary. Primary mirror 22 not only collects the rays but because of its specific concave curvature (ellipsoidal) also redirects the rays so that all of the collected rays enter secondary "conical" mirror 24, positioned at a well defined location in the mirror system (at one focus of a hemi-ellipsoid).

Primary mirror 22 is an ellipsoidal mirror that has focusing properties that are addressed in a paper entitled "Focusing Properties of Hemispherical and Ellipsoidal Mirror Reflectometers", W. M. Brandenberg, Jour. of Optical Soc. of America, Vol. 54, No. 12, pp. 1235–1237, October 1964 and in a paper entitled "Reflectometer Design Using Nonimaging Optics", Keith A. Snail, Applied Optics, 1987.

Secondary mirror 24 has an interior reflective surface surrounding a cavity or open space, this surface has the function of funneling all, or virtually all, of incident radiation onto detector 28 closing the lowermost end of the mirror cavity so that detector response characteristics benefit from the manner in which radiation reaches the detector surface. Mirror 24 accepts radiation originating in the "hemisphere" above mirror 24 and traveling in any direction therefrom into a mirror cavity defined by a reflective wall-like surface open at top and bottom to form a "cone-like" mirror element. Mirror 24 can, as illustrated, funnel one or more rays "directly" to the detector surface so that these rays never strike the mirror surface. Mirror 24 can, as illustrated, funnel one or more rays "indirectly" to the detector surface, causing redirection of rays in the direction of the detector surface after these rays have struck the mirror surface. This redirection is accomplished in a beneficial manner in that the reflected rays leaving the mirror surface are redirected so that the incidence angles of the rays at the detector surface are within a limited number of degrees, typically 20–70 degrees, depending on the detector, of a line perpendicular to the detector surface.

Mirror 24 is rotationally symmetric, having a small aperture at its upper end and a large aperture at its lower end. The upper end of mirror 24 lies in plane shared by a sample 28 because this plane contains two foci of mirror 22 in a manner to be later explained.

Detector 28 can be a detector having a conventional angular response to incident radiation and, as such, can produce an output signal of a strength proportionate to the sum of the intensity of all of the incident radiation of various incidence angles, "weighted" by the detector response at that angle. Such a detector works well together with mirror 24 because these two elements have complementary characteristics. Typically detector 28 has a spatially uniform response characteristic. In turn, mirror 4 works well with mirror 22 because these mirrors have complementary functions in terms of handling electromagnetic energy rays. Because system 20 works best when mirror 24 and detector 28 constitute a spatially uniform black body from which electromagnetic radiation energy, of whatever wavelength, does not escape because detector reflectance is zero (or close to zero), it is considered desirable, although not altogether necessary, that the detector surface be coated with an "antireflection coating", not shown, so that any tendency of the detector surface to reflect rays back into system 20 via mirror 24, is positively defeated. Where, for some reason, an "antireflection coating" is not utilized, or would be only partially effective, there may be other, alternative ways to ensure that such an ideal black body system is attained, or at least approximated.

A radiation beam can be brought to a sample 26 in the following manner. A flat mirror 36 located in predefined relation to movable flat mirror 32 and the site or location where a sample 26 is placed when occasion arises is utilized in the system configuration of FIG. 2. Mirror 32 is mounted on a swivel (not shown) for tilting about an axis, so that mirror 32 can be tilted ninety (90) degrees from its shown position whenever one desires to direct beam 30 to flat mirror 36 and to redirect beam 30 from flat mirror 36 toward the location where a sample 26 can be positioned (or is positioned in some instances). Mirrors 32 and 34 and likewise mirrors 32 and 36 are used to deliver a radiation beam to the site where a sample 26 is placed whenever occasion arises, usually when sample diffuse reflectance is to be measured. Other ways of delivering a beam to a sample 26 or to the sample site can be utilized and mirrors 32, 34, and 36 are merely an exemplary beam-handling system. For example, a hole could be formed in primary mirror 22 and a beam could be directed through the hole at the sample or sample site. In such an instance the mirrors 32, 34 and 36 could be eliminated entirely from the system.

Having thus observed all of the system elements shown in FIG. 2 and most of the elements shown in FIG. 3 please refer further to FIG. 3 showing system 20 reconfigured to include a fixed flat mirror 38 located beneath mirror 24 to direct an incoming beam 30 from a radiation source (not shown) upwardly onto the entire larger aperture of mirror 24 where rays funnel through mirror 24, in a manner indicated in FIG. 3, and leave the smaller aperture of mirror 24 to strike mirror 22 at various points where mirror 22 in turn redirects the radiation onto sample 26. The intensity of the radiation source must be kept constant during both sample in and sample out (or reference) measurements, and the acceptance angle of the CPC mirror must be no larger than the beam divergence. Ideally, sample 26 is bombarded by Lambertian radiation over the entire part of it's surface to be measured. Sample 26, in turn, diffusely reflects the rays incident thereon, with some of these reflected rays reaching flat mirror 34 then flat mirror 32 before striking a radiation detector (not shown) placed across the path of beamed radiation leaving mirror 32.

In the system configuration of FIG. 3, a detector, similar to detector 28 shown in FIG. 2, is placed with its detector surface intercepting collimated, or nearly-collimated rays of a beam leaving mirror 32 and approaching the detector normal or near-normal to the detector surface so that the detector operates in an efficient manner. Whenever the "location" to be occupied by a sample is in fact unoccupied, beam 30' will pass through this "location" on the way to mirror 36 where the beam is redirected toward flat mirror 32, tilted 90 degrees from the shown position, which redirects the beam toward a radiation detector (not shown). Mirrors 32, 34 and 36 form a particular beam handling system as stated earlier but there are other ways to handle a beam.

System 20 of FIGS. 2 and 3 forms but two of many possible embodiments of the invention which typically include a radiation source, a primary mirror, a secondary mirror, and a radiation detector. System 20 differs from other invention embodiments in that primary mirror 22 is ellipsoidal mirror. This primary three demensional (3-D) mirror has two noncoincident foci spaced apart on a major axis of a hemi-ellipsoidal figure defined by a reflective surface, with one mirror focus spatially coincident with the location where a sample 26 is placed, on occasion, and with another mirror focus spatially coincident with the location where the smaller aperture at the top end of secondary mirror 24 is placed in a manner to be described with great particularity because system geometry is a vital concern to those who would construct system 20. Mirror 24 forms a "conical" reflective surface that is rotationally symmetric to funnel radiation in a particular manner. Mirror 22 is, in the example system, a mirror known to the world as a "compound parabolic concentrator", sometimes called a 3d- "CPC" because of its three-dimensional (3d) property. Information on mirror 22 can be found in a text entitled "The Optics of Nonimaging Concentrators, Light and Solar Energy", W. T. Welford, R. Winston, Academic Press, New York, 1978. The 3d- "CPC" (24) forms a rotationally symmetric mirror surface on the inner surface of a longitudinally tapered cavity which is terminated by two apertures which are perpendicular to the axis of rotation. The cavity diameter decreases in an axial direction running from a larger lowermost aperture to a smaller uppermost aperture of the cavity (as shown in FIGS. 2 and 3). A large circular opening formed by the lowermost larger end of the cavity and a small circular opening formed by the uppermost smaller end of the cavity combine with the shape of the mirrored surface to give the "CPC" 24 a shape specified exactly by Winston and Welford. Due to the choice of the CPC acceptance angle, the range of incidence angles on detector 28 (FIG. 2) is limited to angles in the detector's constant response region. See the earlier cited paper(s) by Keith A. Snail.

System 20, as shown in FIGS. 2 and 3, utilizes CPC 24 by placing the small circular opening (of area $A_2$) of CPC 24 at a focus of mirror 22 in fixed relation and area $A_1$ of the irradiated area of sample 26 at the other focus of mirror 22 because this arrangement ensures that all diffusely reflected radiation leaving sample 26 bounces from mirror 22 and fills the smaller aperture of mirror 24 without creating stray radiation that would be lost if mirror 24 where "overfilled". Sizing of the smaller aperture of mirror 24 is determined by the formula $A_1/A_2 \leq 1/\sin^2 \theta_c$ where $A_2$ is the entrance aperture a 24, $A_1$ is the exit aperture area, and $\theta_c$ is the half-angle of radiation incident on the detector 28 placed at $A_1$. The half-angle $\theta_c$ should be equal to the angle at which the detector response begins to fall-off from the normal incidence value, but should preferably not be smaller than 20°. The formula assumes that the media surrounding the source (30) and the detector (28) are air and that radiation enters mirror 24 over a full hemisphere. The above-mentioned Snail paper titled "Reflectometer Design Using Non-imaging Optics" explicitly discusses sizing of the mirror 24 apertures. In the system configuration of FIG. 2, detector 28 fits into the larger aperture (of area $A_1$) or opening of "CPC" 24 so that no rays escape from "CPC" 24 without illuminating detector 28, and detector 28 operates in as efficient a manner as possible.

Figure 4:
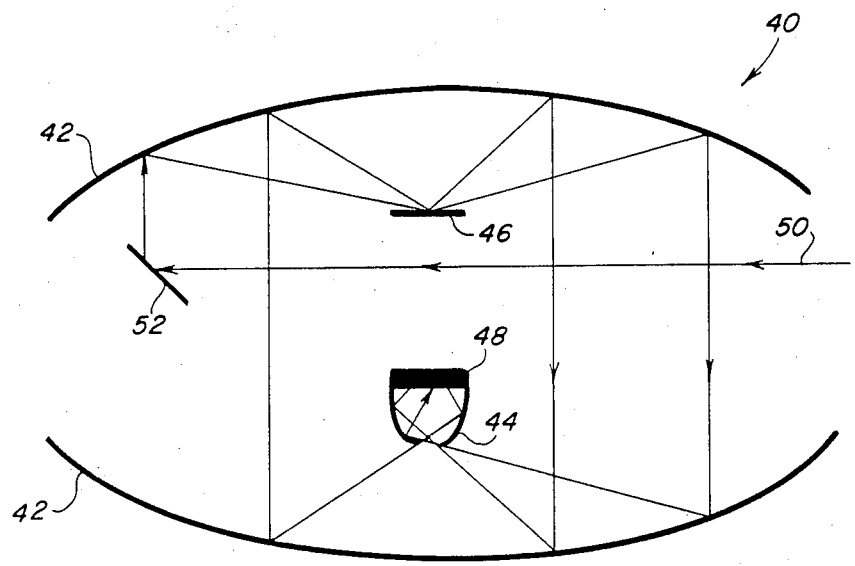
FIGS. 4 and 5 are schematic diagrams of preferred embodiments of the invention incorporating a compound parabolic concentrator and two paraboloidal mirrors.
Figure 5:
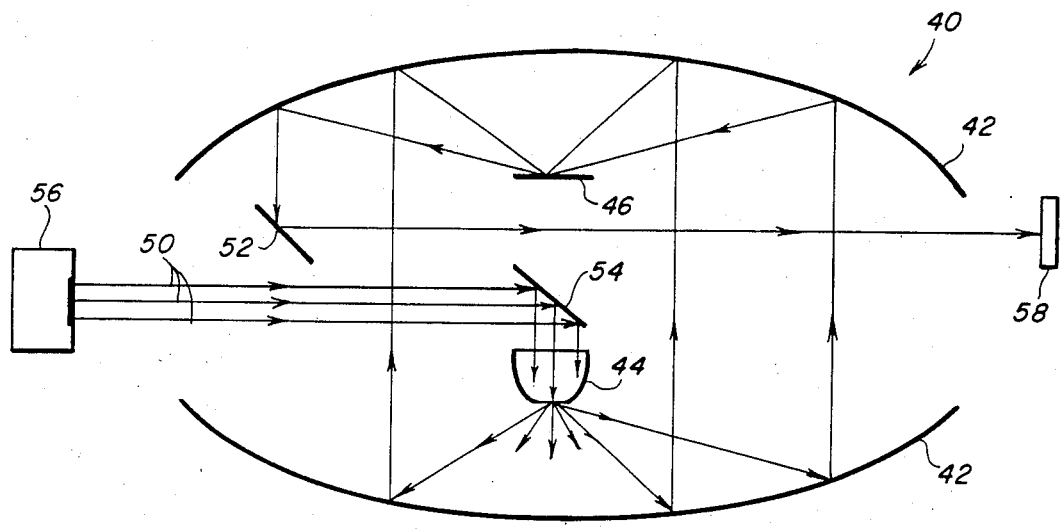

Referring now to FIGS. 4 and 5, an illustrated system 40 representing two further embodiment of the invention is shown to be a system operable in two different configurations. System 40, like system 20, includes a radiation source, a primary mirror, a secondary mirror, and a radiation detector arranged in a precisely defined geometry. System 40, as shown in FIG. 4, includes a two-part primary mirror 42, used as a "collector" mirror, a secondary mirror 44, used as a "detector" mirror, a sample 46 whose diffuse reflectance can be measured by using system 40, and a radiation detector 48 receiving radiation passing through "detector" mirror 44.

A radiation source, represented by a radiation beam 50, produces a beam, coming from the right, that strikes a movable flat mirror 52 where beam 50 is reflected and redirected so that all of the rays of beam 50 striking mirror 52 strike sample 46 when sample 46 is, as shown, carefully located in well defined relation to the locations of "collector" mirror 42 and "detector" mirror 44.

In system 40, primary mirror 42 is actually two mirrors having the function of collecting all, or virtually all, of the rays that are diffusely reflected by sample 46 when properly located. This is illustrated in FIG. 4 by various rays shown scattering in many directions from a sample surface to strike the two mirrors of mirror 42 at many points, represented in FIG. 4 by only three points where the rays are reflected ultimately toward mirror 44 because of the specific concave curvatures (parabolic) of two reflective surfaces of mirror 42. Primary mirror 42 not only collects the rays leaving sample 46, but also redirects the rays so that all of the collected rays enter the cavity of secondary mirror 44, positioned at a well defined location in the mirror system. No rays are lost as stray radiation due to the interaction of mirrors 42 and 44.

Mirror 42 is a dual paraboloidal mirror comprised of an uppermost mirror surface portion and a lowermost mirror surface flanking a space containing sample 46, mirror 52, mirror 44, and detector 48.

Secondary mirror 44 has the function of funneling all, or virtually all, of the incident rays onto detector 48 so that detector response characteristics benefit from the manner in which rays reach the detector surface. Mirror 44, like mirror 24 of system 20, has a wide acceptance angles and accepts rays traveling from many directions into the mirror cavity. Mirror 44 can funnel rays directly to the detector surface so that some rays never strike the mirror and can, as illustrated, funnel rays indirectly to the detector surface causing redirection of rays reflected by mirror 44 in the direction of the detector surface when the rays strike the mirror surface. This redirection is accomplished in a beneficial manner in that the reflected rays leaving the mirror surface are redirected so that the incidence angles of the rays at the detector surface are within a limited number of degrees of a line perpendicular to the detector surface even though the rays enter the mirror cavity from any direction within the hemisphere.

In system 40, detector 48 can be a detector having a conventional angular response to incident radiation and, as such, can produce an output signal of a strength proportionate to the sum of the intensity of all of the incident rays of various incidence angles weighted by the detector response at that angle. Such a detector works well together with mirror 44 because these two elements have complementary characteristics, just as mirror 24 and detector 28 in system 20 have complementary characteristics. In turn, mirror 42 works well with mirror 44 because these mirrors have complementary functions in terms of handling rays. Because system 40 works best when mirror 44 and detector, 58 constitute a spatially uniform, black body from which electromagnetic radiation energy does not escape, it is usually desirable that the detector surface be coated with an "antireflection coating" (not shown) so that any reflection or radiation back into system 40 via mirror 44 does not occur.

Having thus observed all of the system elements shown in FIG. 4 and most of the elements shown in FIG. 5, please refer further to FIG. 5 showing system 40 modified to include a fixed flat mirror 54 located above mirror 44 to direct a diffuse beam 50' from a radiation source 56 into mirror 44 where diverging rays funnel through a mirror cavity, in the manner indicated in FIG. 5, to hereafter strike dual paraboloidal mirror 42 which, in turn redirects the rays onto sample 46 because of the concave curvature of the mirror reflective surfaces. Sample 46, in turn, diffusely reflects the rays incident thereon, with some of these reflected rays reaching flat mirror 52 before striking radiation detector 58 placed across the path of a beam leaving mirror 52 after having been diffusely reflected by sample 46.

System 40 of FIGS. 4 and 5 forms but two of many possible embodiments of the invention, and differs from other embodiments in that primary mirror 42 is a "dual-paraboloidal" mirror. This mirror has two noncoincident foci spaced along the major axis of a dual-paraboloidal figure defined b the mirror, with one mirror focus coincident with the location where a sample is placed, as occasion demands and with another mirror focus coincident with the location where secondary mirror 44 is placed. Mirror 44 is a "compound parabolic concentrator", sometimes called a 3d- "CPC". The 3d- "CPC" (44) is identical in shape to 3d- "CPC" 24 earlier described with reference to the system 20 of FIGS. 2 and 3.

System 40, as shown in FIGS. 4 and 5, utilizes "CPC" 44 by placing the small circular aperture of "CPC" at a focus of dual paraboloidal mirror 42 in fixed relation to sample 46 which is at the other focus of mirror 42. The small aperture of CPC 44 faces the lowermost reflective surface of mirror 42 while sample 46 faces the uppermost reflective surface of mirror 42.

In the system configuration of FIG. 4, detector 48 fits into the larger opening at the larger end of the tapered cavity defined by CPC 44 where detector 48 operates in as efficient a manner as possible because of its association with CPC 44. (The smaller aperture is sized to collect all or virtually all of the radiation reflected from the sample.) In the alternate system configuration of FIG. 5, detector 58, similar to detector 28, is placed with its detector surface intercepting radiation leaving mirror 52. Detector 58 operates in an efficient manner because of the combined effect of mirrors 42 and 44 and sample 46 on the beam 50' coming from source 56 and diffusely reflected by sample 46. The acceptance angle of the mirror 44 (CPC) must be no larger than the beam divergence, and the beam should uniformly fill the mirror's (CPC's) larger aperture.

Figure 6:
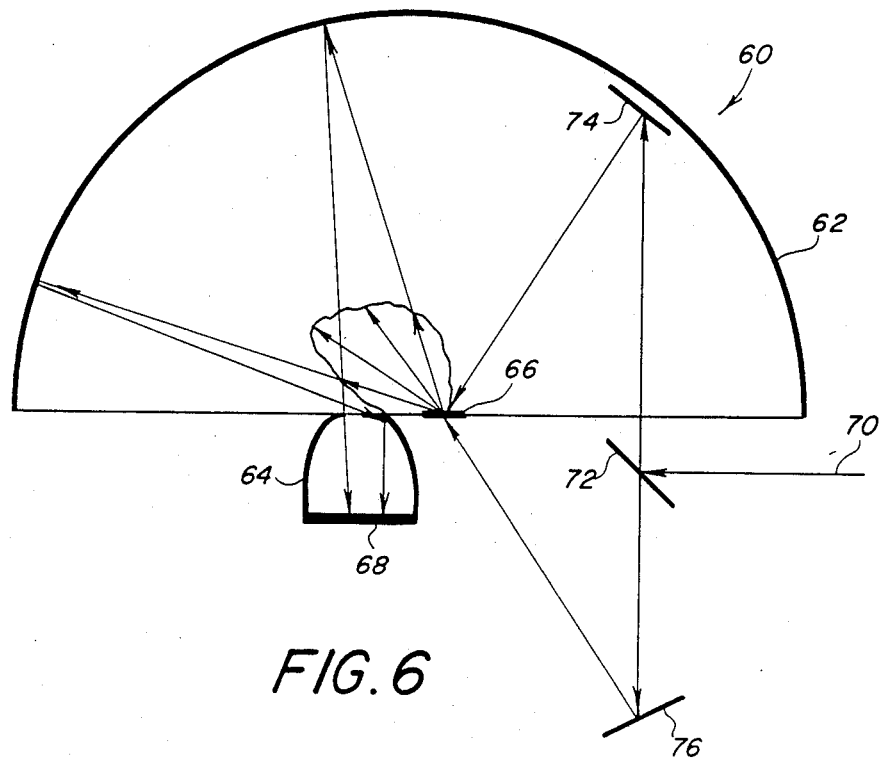
FIGS. 6 and 7 are schematic diagrams of preferred embodiments of the invention incorporating a compound parabolic concentrator (CPC) and a hemispherical mirror.
Figure 7:
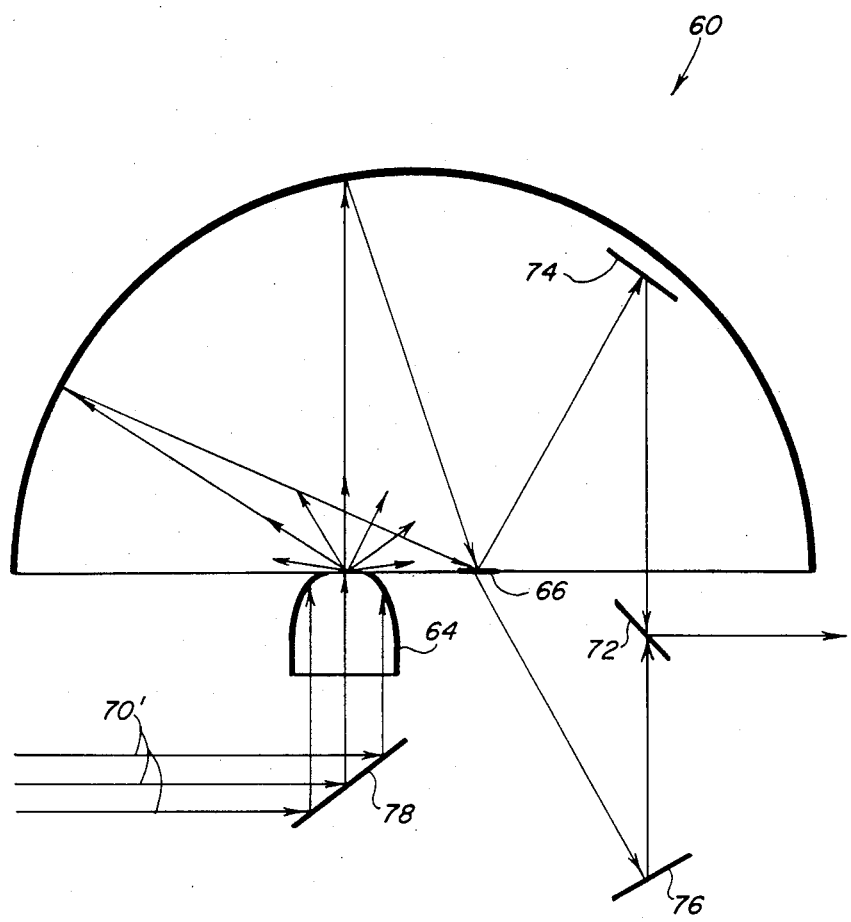

Referring now to FIGS. 6 and 7, the illustrated system 60 represents two additional embodiments of the invention. System 60 has two alternate configurations involving rays routed through a mirror system in the process of irradiating a test specimen or a site where a test specimen can be placed when reflection measurements (specular and/or diffuse) are to be taken. System 60, as shown in FIG. 6, includes a concave primary mirror 62, used as a "collector" mirror, a secondary mirror 64, used as a "detector" mirror, a sample 66 whose reflectance is to be measured, and a detector 68 receiving rays coming from "detector" mirror 64. The four components 62, 64, 66 and 68 define a system geometry with mirrors 62 and 64 having geometry crucial to a successful practice of the invention embodiments.

A radiation source, represented by an incoming beam 70, provides a beam, coming from the right, and strikes a tiltable flat mirror 72 where beam 70 is redirected to another flat mirror 74 where beam 70 is again redirected so that all of the rays of beam 70 strike sample 66 where the rays are diffusely reflected and radiate into a hemispherical cavity defined by the reflective surface of mirror 62 which is a hemispherical mirror.

In system 60, primary mirror 62 has the function of collecting all, or virtually all, of the radiation reflected by a sample. This is illustrated in FIG. 6 by various rays shown scattering in many directions from a sample surface to strike mirror 62 at many points, represented in FIG. 6 by only two points, where the rays are reflected in the direction of secondary mirror 64 and the associated detector 68. Primary mirror 62 not only collects the rays but also redirects the rays so that all of the collected rays enter a cavity formed by secondary mirror 64. The Brandenburg paper cited above provides information on the focusing properties of a hemispherical mirror(62).

Secondary mirror 64 has the function of funneling all, or virtually all, of the incident rays onto detector 68 so that detector response characteristics benefit from the manner in which rays reach the detector surface. Mirror 64 accepts rays traveling from many directions into mirror 64. Mirror 64 as illustrated, funnel rays "directly" to the detector surface so that some rays never strike the mirror. Mirror 64, as illustrated, funnel rays "indirectly" to the detector surface, causing redirection of rays in the direction of the detector surface after the rays have struck the mirror surface. This redirection is accomplished in a beneficial manner in that the reflected rays leaving the mirror surface are redirected so that the incidence angles of the rays at the detector surface are within a limited number of degrees of a line perpendicular to the detector surface thus reducing or eliminating variations in response due to the Fresnel reflectance of detector surface.

Detector 68 can be a detector having a conventional angular response to incident radiation and, as such, can produce an output signal of a strength proportionate to the sum of the intensity of all of the incident rays of various incidence angles weighted by the response of the detector at each angle. Such a detector works well together with mirror 64 because these two elements have complementary characteristics as described herein. In turn, mirror 62 works well with mirror 64 because these mirrors have complementary functions in terms of handling rays as described herein. System 60 works best when the response of detector 68 is spatially uniform and the reflectance constitutes a black body wherein detector 68 does not allow electromagnetic radiation energy, of wavelength of interest, to escape. The detector surface may be coated with an "antireflection coating" to defeat any tendency of the detector surface to reflect rays back into system 60 via mirror 64. Where an "antireflection coating" is not utilized, a grey body rather than a black body system may result that would suit some system applications.

A flat mirror 76 located in the shown relation to flat mirror 72 and the location where a sample 66 is placed, when occasion arises, is used in system 60. Mirror 72 can be tilted ninety (90) degrees from the position shown in FIG. 6 to redirect beam 70 from mirror 72 to mirror 76 to the site or location where a sample 66 is sometimes positioned. Ordinarily, mirror 76 is so used when there is no sample at the indicated position because an operator needs to take "absolute" reference measurements of incoming radiation.

Having thus observed all of the system elements shown in FIG. 6 and most of the elements shown in FIG. 7, please refer further to FIG. 7 showing a alternate system configuration that includes a fixed flat mirror 78 located below mirror 64 to direct a divergent radiation beam 70 onto the larger aperture of mirror 64 where diffuse rays funnel through the mirror cavity, in the manner indicated in FIG. 7, to leave mirror 64 in many directions to strike mirror 62 which, in turn redirects the rays in a Lambertian manner onto sample 66 located at the designated site. Sample 66, in turn, diffusely reflects the rays incident thereon, with some of these reflected rays reaching stationary flat mirror 74 then flat mirror 72 before striking a detector (not shown) placed in the path of an exit beam processed by sample 66 and by mirrors 62 and 64.

System 60 (FIGS. 6 and 7) forms a two additional embodiments of the invention, and differs from the earlier described embodiments in that primary mirror 62 is a hemispherical mirror. This mirror has two coincident foci at the very center of a sphere containing the hemispherical mirror. The centers of sample 66 and secondary mirror 64 are placed on the same circle diameter of the hemisphere's base plane. Sample 66 and mirror 64 are placed as close as possible to the center of the hemisphere. Mirror 64 is a "compound parabolic concentrator", or "CPC" which has been described with reference to systems 20 and 40. System 60, as shown in FIGS. 6 and 7, utilizes "CPC" 64 by placing the small circular aperture of "CPC" 64 in fixed relation to mirror 62 and to a sample 66.

In the system configuration of FIG. 6, detector 68 fills the larger circular aperture of the 3d- "CPC" 64. No rays can escape from "CPC" 64 without illuminating detector 68. In the system configuration of FIG. 7, a detector not shown but similar to detector 68 is placed with its detector surface intercepting collimated, or nearly-collimated radiation leaving mirror 72. The detector operates in an efficient manner because mirrors 62 and 64 are utilized together with sample 66 or together with the unoccupied sample site.

A few additional observations may aid in clarifying details of systems 20, 40 and 60. Detectors have maximum response when radiation incidence angle ($O_c$) is zero degrees. Detectors presently have maximum response when said incidence angles range from approximately 20 to 70 degrees of a line normal to the detector surface whereas rays entering the entry apertures of CPC mirros 24, 44 and 64 may have incidence angles as high as ninety (90) degrees. The size of mirrors 24, 44 and 64 are determined by the aforesaid relationship $A_1/A_2 \leq 1/\sin^2 O_c$ wherein area $A_1$ is the exit aperture which is equal to the irradiated surface area of the detectors 28, 48, and 68 in systems 20, 40 and 60 as previously described. The area of aperture $A_2$ is chosen such that the image of the sample is always smaller than and contained within $A_2$. Mirror 22 in system 20 although elliptical as described above is drawn as a hemisphere, and thus resembles the hemispherical mirror 62 in system 60 to emphasize the fact that although systems 20 and 60 involve specifically different geometries the radiation processing effect of the two systems is the same (and is the same as that of system 40). FIGS. 1-7 of the drawings are not drawn to scale so that the described system geometries unavoidably are represented in the Figs. with a degree of distortion. For example, mirrors 24, 44 and 64 of systems 20, 40, and 60, which are identical in shape, can also be identical in size, even though mirror 44 as shown appears smaller than mirrors 24 and 64. The entrance aperture of mirrors 24 and 64 are in a plane common to samples 26 and 66 respectively. The entrance aperture of mirror 44 and the irradiated surface of sample 46 are disposed normal to a plane passing through their two centers where the two foci of mirror 42 are disposed.

In system 20, 40 and 60, the CPC mirrors 24, 44 and 64 are used with detectors 28, 48 and 68 respectively to construct systems 20, 40 and 60 in which detector response is nearly independent of angle. This is accomplished by filling the larger aperture of each CPC mirror with a detector and then choosing the CPC half angle, $O_c$, to correspond to the flat part of the detector's angular response function.

Obviously, numerous (additional) modifications and variations of the invention are possible in light of the above teachings. It is therefore to be understood that within the scope of the appended claims, the invention any be practiced otherwise than as specifically described.

What is claimed and desired to be secured by letters patent of the United States is:

1. A system for measuring diffuse reflectance of radiation by a sample, comprising:
    a "collector" mirror having a "hemispherical" concave mirror surface;
    a compound parabolic concentrator as a paraboloidal "detector" mirror having a rotationally symmetric, paraboloidally tapered mirror surface surrounding a mirror cavity communicating with respective apertures formed at opposite ends of this mirror surface by circular ends of this mirror surface, one end of this mirror surface forming a small circular aperture of area $A_2$, another end of this mirror surface forming a large circular aperture of area $A_1$;
    a detector having a characteristic detector response to incident radiation arriving at the detector over a wide range of incidence angles so that detector response falls off from normal incidence value when radiation with large incidence angles is detected, the detector being positioned at the large circular aperture formed at one circular end of the mirror surface of the "detector" mirror so that an area of the detector coextensive with the area $A_1$ of the large circular aperture receives incident radiation, the ratio of area $A_1$ divided by area $A_2$ being less than or equal to 1 divided by $\sin^2\theta_c$ where $\theta_c$ is the half angle of radiation incident on the detector;
    the "collector" mirror and the "detector" mirror and the detector being arranged into a reflectometer system in which the concave mirror surface aligns with the "detector" mirror so that the concave mirror surface can reflect radiation toward the small aperture of the "detector" mirror and so that the large aperture of the "detector" mirror can funnel radiation onto the detector;
    means for continously directing a beam of radiation onto the surface area of a sample in a manner such that all radiation directed to the surface area can be collected by the "collector" mirror despite the diffuse reflectance of the surface area and so that the concave mirror surface reflects all collected radiation through the small aperture into the mirror cavity where some of the radiation travels straight through the cavity to exit the large aperture and impinge on the detector and where the rest of the radiation is reflected by the tapered mirror surface before exiting the mirror cavity via the large aperture to impinge on the detector; and
    the detector and the "detector" mirror constituting a means for detecting the radiation forwarded from the sample via the mirrors to the detector to obtain an optimum detector response which is independent of the incidence angles of the radiation arriving at the small aperture because the tapered mirror surface redirects radiation having large incidence angles at the small aperture so that this radiation has reduced incidence angles upon arriving at the detector after exiting the mirror cavity via the large aperture.

2. The system of claim 1 wherein the "collector" mirror is a mirror having a hemi-ellipsoidal mirror surface.

3. The system of claim 1 wherein the "collector" mirror is a mirror having two paraboloidal mirror surfaces facing each other so that one of these mirror surfaces aligns with the "detector" mirror so serve as concave mirror surface in the manner recited and the remaining one of these mirror surfaces passes radiation coming from the diffusely reflecting surface area of the sample to the mirror surface aligned with the "detector" mirror.

4. The system of claim I wherein the "collector" mirror is a mirror having a hemispherical mirror surface.

5. The system of claim 1 wherein the means for continuously directing a beam of radiation onto the surface area of the sample is a beam-handling system separate and distinct from the mirrors.

6. A method of measuring diffuse reflectance of radiation by a sample, comprising the steps of:
    providing a "collector" mirror having a "hemispherical" concave mirror surface;
    providing compound parabolic concentrator as a paraboloidal "detector" mirror having a rotationally symmetric, paraboloidally tapered mirror surface surrounding a mirror cavity communicating with respective apertures formed at opposite ends of this mirror surface by circular ends of this mirror surface, one end of this mirror surface forming a small circular aperture of area $A_2$, another end of this mirror surface forming a large circular aperture of area $A_1$;

providing a detector having a characteristic detector response to incident radiation arriving at the detector over a wide range of incidence angles so that detector response falls off from normal incidence value when radiation with large incidence angles is detected, and positioning the detector at the large circular aperture formed at one circular end of the mirror surface of the "detector" mirror so that an area $A_1$ of the detector can receive incident radiation, the ratio of area $A_1$ divided by $A_2$ being less than or equal to 1 divided by $\sin^2\theta_c$ where $\theta_c$ is the half angle radiation incident on the detector;

arranging the "collector" mirror and the "detector" mirror and the detector into a reflectometer system in which the concave mirror surface aligns with the "detector" mirror so that the concave mirror surface can reflect radiation toward the small aperture of the "detector" mirror and so that large aperture of the "detector" mirror can funnel radiation onto the detector;

continuously directing a beam of radiation onto the surface area of a sample in a manner such that all radiation directed to the surface area can be collected by the "collector" mirror despite the diffuse reflectance of the surface area and so that the concave mirror surface reflects all collected radiation through the small aperture into the mirror cavity where some of the radiation travels straight through the cavity to exit the large aperture to impinge on the detector and where the rest of the radiation is reflected by the tapered mirror surface before exiting the mirror cavity via the large aperture to impinge on the detector; and detecting the radiation forward from the sample via the mirrors to the detector to obtain an optimum detector response which is independent of the incidence angles of the radiation arriving at the small aperture because the tapered mirror surface redirects radiation having large incidence angles at the small aperture so that this radiation has reduced incidence angles upon arriving at the detector after exiting the mirror cavity via the large aperture.

7. The method of claim 6 wherein the step of providing the "collector" mirror is performed by providing a mirror having a hemi-ellipsoidal mirror surface.

8. The method of claim 6 wherein the step of providing the "collector" mirror is performed by providing a mirror having two paraboloidal mirror surfaces facing each other so that either one of these mirror surfaces can be aligned with the "detector" mirror to serve as the concave mirror surface in the manner recited and the remaining one of these mirror surfaces can be used to pass radiation coming from the diffusely reflecting surface area of the sample to the mirror surface aligned with the "detector" mirror.

9. The method of claim 6 wherein the step of providing the "collector" mirror is performed by providing a mirror having a hemispherical mirror surface.

10. The method of claim 6 wherein the step of continuously directing a beam of radiation onto the surface area of the sample is performed by using a beam-handling system separate and distinct from the mirrors.

* * * * *